United States Patent [19]

Duchesne et al.

[11] Patent Number: 5,256,803
[45] Date of Patent: Oct. 26, 1993

[54] PROCESS FOR THE PREPARATION OF (2R,3R)-CIS-β-PHENYLGLYCIDIC ACID

[75] Inventors: Jean-Pierre Duchesne, Lyons; Michel Mulhauser, Ecully, both of France

[73] Assignee: Rhone-Poulenc Rorer S.A., France

[21] Appl. No.: 920,509

[22] PCT Filed: Feb. 20, 1991

[86] PCT No.: PCT/FR91/00133
§ 371 Date: Aug. 21, 1992
§ 102(e) Date: Aug. 21, 1992

[87] PCT Pub. No.: WO91/13066
PCT Pub. Date: Sep. 5, 1991

[30] Foreign Application Priority Data

Feb. 21, 1990 [FR] France ................ 90 02098

[51] Int. Cl.$^5$ ................ C07D 301/32; C07D 303/12
[52] U.S. Cl. ................ 549/541; 549/549
[58] Field of Search ................ 549/541, 549

[56] References Cited

U.S. PATENT DOCUMENTS 3,901,915  8/1975  Perry et al. ................ 549/549

FOREIGN PATENT DOCUMENTS

| 110683 | 7/1981 | Japan | 549/549 |
| 13775 | 1/1985 | Japan | 549/549 |
| 145174 | 7/1986 | Japan | 549/549 |
| 226881 | 9/1989 | Japan | 549/549 |
| 2244055 | 11/1991 | United Kingdom | 549/541 |
| 10002 | 9/1990 | World Int. Prop. O. | 549/549 |

*Primary Examiner*—Joseph E. Evans
*Attorney, Agent, or Firm*—Morgan & Finnegan

[57] ABSTRACT

A method for preparing β-phenylglycidic-(2R, 3R) acid optionally in the form of salt or ester by precipitation of the salt of the β-phenylglycidic-(2R,3R) acid with (+)-α-methylbenzylamine-(R) in a solution of a mixture of salts of cis and trans β-phenylglycidic acids with (+)-α-methylbenzylamine(R)- and the use of the resulting product for preparing taxol and its analogs.

6 Claims, No Drawings

PROCESS FOR THE PREPARATION OF (2R,3R)-CIS-β-PHENYLGLYCIDIC ACID

FIELD OF THE INVENTION

The present invention relates to a new process for the preparation of (2R,3R)-β-phenylglycidic acid of formula:

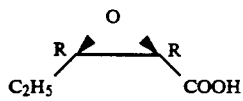

optionally in salt or ester form.

BACKGROUND OF THE INVENTION

Products of general formula (I) can be employed to prepare taxol under the conditions described in papers by J-N. Denis et al., J. Org. Chem., 51, 46–50 (1986); J. Amer. Chem. Soc., 110, 5917–5919 (1988) or the taxol derivatives which are described in European Patent EP 253,738.

It is known, in particular according to J-N. Denis et al., J. Org. Chem., 51, 46–50 (1986), to prepare the products of general formula (I) by titanium-catalyzed asymmetric epoxidation (T. Katsuki and K. B. Sharpless, J. Amer. Chem. Soc., 102, 5974–5976 (1980); J. G. Hill et al., J. Org. Chem., 48, 3607 (1983)) of cis-cinnamic alcohol, followed by oxidation and esterification of the epoxyalcohol obtained. However, the yields are not satisfactory, the enantiomer excesses are generally lower than 80% and the route is relatively long.

According to K. Harada, J. Org. Chem., 31, 1407–1410 (1966), it is known to separate the isomers of trans-β-phenylglycidic acid by precipitation of a salt with optically active α-methylbenzylamine.

According to K. Harada and Y. Nakajima, Bull. Chem. Soc. Japan, 47 (11) 2911–2912 (1974), it is known to separate the isomers of cis-β-phenylglycidic acid by precipitation of a salt with optically active ephedrine.

Application EP 0,342,903 describes the separation of an enantiomer of β-(4-methoxyphenyl)glycidic acid from the corresponding diastereomer by means of optically active α-methylbenzylamine.

However, to make it possible for these processes to be carried out, the cis and trans isomers of β-phenylglycidic acid must be separated beforehand.

It has now been found, and it is this that forms the subject of the present invention, that (2R,3R)-β-phenylglycidic acid can be obtained from a mixture of the cis and trans isomers.

DESCRIPTION OF THE INVENTION

The process according to the invention consists in crystallizing in a suitable solvent the salt of (2R,3R)-β-phenylglycidic acid with the (R)(+)-α-methylbenzylamine present in a mixture of (R)(+)-α-methylbenzylamine salts with (2R,3R)-β-phenylglycidic acid, (2S,3S)-β-phenylglycidic acid, (2R,3S)-β-phenylglycidic acid and (2S,3R)-β-phenylglycidic acid.

Solvents which may be employed are water or an organic solvent chosen from aliphatic alcohols containing 1 to 4 carbon atoms, such as methanol or ethanol, ethers or ketones, optionally mixed with water.

The precipitation of the salt of (2R,3R)-β-phenylglycidic acid with (R)(+)-α-methylbenzylamine is generally performed by adding acetone to an aqueous or organic, preferably ethanolic, solution of the mixture of the salts of the optical isomers of cis and trans β-phenylglycidic acids with (+)-α-methylbenzylamine.

When the operation is performed in organic medium, it is particularly advantageous to add the acetone to the organic solution at reflux and then to make the desired salt precipitate on cooling.

When the operation is performed in aqueous medium, it is particularly advantageous to add the acetone until a mixture containing from 25 to 50% of water and from 75 to 50% of acetone is obtained. The best results are preferably obtained when the crystallization solution contains approximately 35% of water and 65% of acetone.

The mixture of the salts of the optical isomers of cis and trans β-phenylglycidic acids with (R)(+)-α-methylbenzylamine can be obtained:

by the action of (R)(+)-α-methylbenzylamine on the mixture of the cis and trans isomers of β-phenylglycidic acid which is prepared in situ, or by the action of a salt of (R)(+)-α-methylbenzylamine, such as the hydrochloride, on the mixture of the alkali metal salts, such as the potassium salts, of cis and trans β-phenylglycidic acids.

The mixture of the alkali metal salts of cis and trans β-phenylglycidic acids can be obtained by saponifying the corresponding esters with an inorganic base. It is particularly advantageous to employ ethanolic potassium hydroxide, the operation being carried out at a temperature close to 20° C. It is not necessary to isolate the esters before the reaction with the inorganic base.

The mixture of cis and trans β-phenylglycidic acids can be obtained in situ by acidifying an aqueous solution of the mixture of the corresponding alkali metal salts.

The mixture of the esters of cis and trans β-phenylglycidic acids can be obtained by the action of an alkyl haloacetate, such as an alkyl chloro- or bromoacetate, on benzaldehyde, according to the method described by F. W. Bacheler and R. K. Bansal, J. Org. Chem., 34 (11) 3600–3604 (1969). It is particularly advantageous to employ t-butyl chloroacetate, which enables a practically equimolar mixture of the cis and trans isomers to be obtained.

By replacing t-butyl chloroacetate with t-butyl bromoacetate and by operating preferably close to 0° C. it is possible to obtain a mixture in which the proportion of cis isomer is close to 75%.

Using the action of an inorganic base, preferably ethanolic potassium hydroxide, on the ester prepared in situ as indicated above, it is possible to precipitate the mixture of the alkali metal salts of cis and trans β-phenylglycidic acids (potassium salts) together with the alkali metal halide (potassium chloride or bromide), which, after isolation, can be treated with an aqueous solution of an (R)(+)-α-methylbenzylamine salt as indicated above.

Whatever the process used to prepare the mixture of the esters of the cis. and trans acids, it is possible to obtain a mixture containing 80% of cis ester and 20% of trans ester by crystallizing the trans isomer in the cis isomer, which acts as the solvent.

The (2R,3R)-β-phenylglycidic acid obtained according to the process of the present invention is particularly useful for preparing the taxane derivatives of general formula:

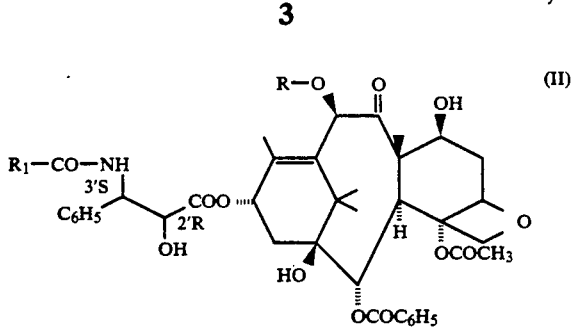

in which R denotes a hydrogen atom or an acetyl radical and $R_1$ denotes a phenyl or t-butoxy radical.

EXAMPLES

The following examples, given without any limitation being implied, show how the invention can be put into practice.

EXAMPLE 1 a) 106 g of benzaldehyde (1 mole), 150.7 g of t-butyl chloroacetate (1 mole) and 450 cm³ of t-butanol are introduced into a 2-liter round bottom flask. A solution of 112.5 g of potassium t-butylate (1 mole) in 850 cm³ of t-butanol is then added over 2 hours 40 minutes at a temperature of between 18° and 24° C. After 18 hours' stirring at a temperature close to 20° C., t-butanol is evaporated off under reduced pressure. The residue obtained is taken up with 1000 cm³ of water. The solution is extracted with 3×300 cm³ of methylene chloride. The combined organic phases are dried over magnesium sulphate. After filtering and concentrating to dryness under reduced pressure, an oil (210 g) is obtained, whose molar composition, determined by the proton nuclear magnetic resonance spectrum, is as follows:
t-butyl cis-β-phenylglycidate: 53%
t-butyl trans-β-phenylglycidate: 42%
t-butyl chloroacetate: 5% b) By operating as before but replacing t-butyl chloroacetate with 195 g of t-butyl bromoacetate (1 mole), an oil (213 g) is obtained, whose molar composition, determined by the proton nuclear magnetic resonance spectrum is as follows:
t-butyl cis-β-phenylglycidate: 63%
t-butyl trans-β-phenylglycidate: 32%
t-butyl bromoacetate: 5%

Into a reactor are introduced 800 cm³ of ethanol and 298 g of a mixture of t-butyl cis-β-phenylglycidate (80%) and of t-butyl trans-β-phenylglycidate (20%), obtained after crystallization at 4° C. for several days and separation of the trans isomer from the mixture of the cis and trans isomers obtained previously in a) or b).

The ethanolic solution is cooled to a temperature close to 0° C. and is then treated for 3 hours with 134 g of 85% potassium hydroxide (2.03 moles) in solution in 600 cm³ of ethanol. After 18 hours' stirring, the reaction mixture is filtered. The solid obtained is washed with 200 cm³ of cold ethanol and is then dried to a constant weight. 185 g of a white solid are thus obtained, whose composition, determined by the proton nuclear magnetic resonance spectrum, is as follows:
potassium cis-β-phenylglycidate: 74%
potassium trans-β-phenylglycidate: 42%

The following are introduced into a reactor:
185 g of potassium β-phenylglycidate obtained previously
625 cm³ of an ice-water mixture
770 cm³ of ethyl ether.

The mixture is cooled to 0° C. At this temperature, 185 cm³ of 5N hydrochloric acid are added over 2 hours. As soon as the addition is finished, the organic and aqueous phases are separated. The aqueous phase is extracted with 2×100 cm³ of ether. The organic phases are dried over sodium sulphate. After filtering, the organic phases are treated with 125 cm³ of (R)(+)-α-methylbenzylamine (0.95 moles) with vigorous stirring. The precipitate formed is separated off by filtration, is washed with 200 cm³ of cold ethyl ether and is then dried. 194 g of a white powder are thus obtained, whose analysis by the proton nuclear magnetic resonance spectrum shows that it consists of 81% of (R)(+)-α-methylbenzylamine cis-β-phenylglycidate and 19% of (R)(+)-α-methylbenzylamine trans-β-phenylglycidate.

193 g of the salt obtained previously and 800 cm³ of ethanol are introduced into a reactor. The mixture is heated to reflux. A colorless homogeneous solution is thus obtained, which is treated at reflux with 1600 cm³ of acetone. The homogeneous solution is allowed to cool to 45° C. and a few crystals of (R)(+)-α-methylbenzylamine (2R,3R)-β-phenylglycidate are then added. As soon as the temperature reaches 42° C. an abundant precipitate forms. Two hours after the end of the addition of acetone the temperature is close to 25° C. The precipitate is separated off by filtration, is rinsed with acetone and is dried to constant weight. 36 g of practically pure (R)(+)-α-methylbenzylamine (2R,3R)-β-phenylglycidate (0.126 moles) are thus obtained.

The enantiomer excess, measured after forming a methyl ester derivative followed by an analysis by chiral HPLC, is 97%.

EXAMPLE 2

28.53 g of (R)(+)-α-methylbenzylamine (2R,3R)-β-phenylglycidate (0.1 mole) obtained in Example 1 and 200 cm³ of dichloromethane are introduced into a reactor. 50 cm³ of 2N potassium hydroxide are added over 20 minutes to the heterogeneous mixture at 22° C. As soon as the addition is finished the two liquid phases are separated. The organic phase is washed with water. The combined aqueous phases are concentrated to dryness. 19.9 g of (2R,3R) potassium β-phenylglycidate whose rotatory power is $[\alpha]_D = 2.8°$ C. =7.4; water) are thus obtained.

EXAMPLE 3

523 cm³ of (R)(+)-α-methylbenzylamine (3.97 moles) and 760 cm³ of ethanol are introduced into a 6-liter round bottom flask. The reaction mixture is cooled externally with an ice-acetone mixture. 143 cm³ of 2.78N hydrochloric acid are added while the temperature is kept below 10° C. The reaction mixture remains clear and colorless.

Into a 10-liter round bottom flask are introduced 3.8 liters of ethanol and 768 g of a product whose composition is as follows:
potassium cis-β-phenylglycidate: 80%
potassium trans-β-phenylglycidate: 12%
potassium chloroacetate: 8%

The solution of (R)(+)-α-methylbenzylamine hydrochloride prepared above is added to the heterogeneous mixture thus obtained, which is heated to 35°–40° C. The reaction mixture is kept at 50° C. for 2 hours. The potassium chloride which precipitates out is separated off by filtration and is washed with boiling methanol.

The filtrate is concentrated to a weight of 2445 g and is then left at room temperature for 18 hours. The crystals which have appeared are separated off by filtration, are washed with 6×200 cm³ ethanol and are dried to constant weight. 530 g of crystals are thus obtained, whose analysis by proton nuclear magnetic resonance spectrum shows that it consists of pure (R)(+)-α-methylbenzylamine cis-β-phenylglycidate whose enantiomer excess is 7%.

525 g of the salt thus obtained are placed in a reactor containing 3.15 liters of ethanol. The mixture is heated to reflux so as to become practically homogeneous. 6.3 liters of boiling acetone and a few crystals of (2R,3R) salt are then added. The material is allowed to cool slowly to room temperature. The crystals which have appeared are separated off by filtration, are washed with 6×200 cm³ of acetone and are dried to constant weight.

217 g of (R)(+)-α-methylbenzylamine (2R,3R)-β-phenylglycidate are thus obtained, whose enantiomer excess is 98.4%.

EXAMPLE 4 a) 17.6 kg of potassium t-butylate are dissolved under nitrogen atmosphere in a mixture of 60 liters of t-butanol and 65 liters of tetrahydrofuran at 30° C. in a stainless steel 170-liter reactor. 134 liters of a solution A are thus obtained.

28.720 kg of t-butyl bromoacetate and 16.2 kg of benzaldehyde in 125 liters of t-butanol are introduced at 20° C. under nitrogen atmosphere into a 250-liter reactor. The mixture is cooled to 0° C. and then solution A is added over 3 hours while the temperature is maintained at 0° C. This temperature of 0° C. is maintained for another 2 to 3 hours.

A solution of 12.480 kg of potassium hydroxide pellets in 50 liters of absolute ethanol is added over 1 hour 20 minutes to the solution obtained, which is kept at 0° C. Vigorous stirring (150 revolutions/minute) is maintained for approximately 20 hours at 20° C. 24 liters of demineralized water are then added, followed by heating to 50° C. over 1 hour 30 minutes, this temperature being then maintained for 10 minutes. The material is cooled to 10° C. over 6 hours and is then filtered under a nitrogen pressure of 2 bars. The filter cake is washed with 3×30 liters and then 20 liters of a mixture of methyl tert-butyl ether and ethanol (1/1 by volume) and is then dried under reduced pressure (1 mm of mercury, 0.13 kPa) at 30° C. 45.58 kg of a product are thus obtained, containing, according to the proton nuclear magnetic resonance spectrum, 57% by weight of a mixture of the potassium salts of cis (73%) and trans (27%) β-phenylglycidic acids and 43% by weight of potassium bromide.

b) 31.86 kg of (R)(+)-α-methylbenzylamine and 12 kg of ice are introduced under nitrogen atmosphere into a 100-liter reactor. The latter is cooled externally to 20° C. and 23.64 liters of concentrated (10.9N) hydrochloric acid are then added over 2 hours while the temperature of the reaction mixture is kept between 20° and 25° C. 65 liters of a colorless clear solution are thus obtained.

Into a 250-liter reactor are introduced, under nitrogen atmosphere, 87.3 kg of the mixture of the potassium salts of cis and trans β-phenylglycidic acids and of potassium bromide, obtained under the conditions described above, and 200 liters of distilled water. The materials are heated to 45° C. until dissolved and are then cooled to 30° C. 20 liters of (R)(+)-α-methylbenzylamine hydrochloride solution are added over 10 minutes. Crystallization is initiated with 13 g of (R,R)-cis salt. Crystallization is instantaneous. The remainder of the (R)(+)-α-methylbenzylamine hydrochloride solution is then added over 15 minutes.

After 1 hour of cooling to 22° C., 17.5 kg of sodium chloride are added and the mixture is stirred for 3 hours. The temperature is 17° C. The material is filtered under a nitrogen pressure of 2 bars. 263 liters of filtrate and 60 liters of cake are obtained. The cake is washed with 2×40 liters of an aqueous solution of sodium chloride at a concentration of 340 g/liter and then 25 liters of sodium chloride solution. 118 liters of washings and 48 liters of cake are obtained. The cake is beaten on the filter with 50 liters of water at 0° C. for 1 hour. 55 liters of filtrate are obtained, and 45 liters of cake, which is dried to constant weight. 34.1 kg of salt of cis-β-phenylglycidic acid with (R)(+)-α-methylbenzylamine are thus obtained practically pure (vapor phase liquid chromatography with derivative formation, proton nuclear magnetic resonance spectrum at 200 MHz, potentiometric determination).

Into a 250-liter enamelled reactor are introduced 51.2 kg of water and 36.4 liters of acetone, followed by 33.7 kg of the salt of cis-β-phenylglycidic acid with (R)(+)-α-methylbenzylamine, assaying at 95% by titration and containing 53.2%, that is 60.4 moles, of 2R,3R product.

The reaction mixture is heated to reflux (63° C.) and is then cooled slowly after initiation by adding 58 g of pure 2R,3R salt.

After several hours at a temperature close to 20° C. the crystals are separated off by filtration and washed with 3×15 liters of a water-acetone mixture (36/64 by volume) and then with 3×15 liters of acetone. After drying to constant weight under reduced pressure (5 mbar) at 30° C., 12.5 kg of the salt of (2R,3R)-cis-β-phenylglycidic acid with (R)-α-methylbenzylamine are obtained pure according to analysis by chiral HPLC.

The yield is 72%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of (2R,3R)-cis-β-phenylglycidic acid of formula:

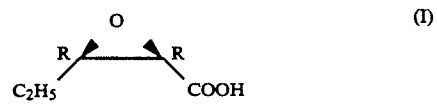

optionally in salt or ester form, comprising crystallizing selectively the salt of (2R,3R)-cis-β-phenylglycidic acid with (R) (+)-α-methylbenzylamine in a suitable solvent in a solution of a mixture of the salts of (R) (+)-α-methylbenzylamine with (2R,3R)-β-phenylglycidic, (2S,3S)-β-phenylglycidic, (2R,3S)-β-phenylglycidic and (2S,3R)-β-phenylglycidic acids, and isolating the product obtained and optionally converting it into alkali metal salt or into ester.

2. Process according to claim 1, wherein the solvent is chosen from water and organic solvents chosen from aliphatic alcohols containing 1 to 4 carbon atoms, ethers and ketones optionally mixed with water.

3. Process according to claim 1, wherein, acetone is added to an aqueous, organic or hydroorganic solution of the mixture of the salts defined in claim 1, and the salt of (2R,3R)-β-phenylglycidic acid with (R) (+)-α-methylbenzylamine is then precipitated and isolated by filtration.

4. Process according to claim 1, wherein a mixture consisting of approximately 80% of the salts of the cis isomer of β-phenylglycidic acid with (R) (+)-α-methylbenzylamine and of approximately 20% of the salts of the trans isomer of β-phenylglycidic acid with (R) (+)-α-methylbenzylamine is employed.

5. Process according to claim 1, wherein the mixture of the salts of (R) (+)-α-methylbenzylamine and the cis and trans isomers of β-phenylglycidic acid is obtained by the action of (+)-α-methylbenzylamine on a mixture of the cis and trans isomers of β-phenylglycidic acid prepared in situ.

6. Process according to claim 1, wherein the mixture of the salts of (R) (+)-α-methylbenzylamine with the cis and the trans isomers of β-phenylglycidic acid is obtained by the action of a salt of (+)-α-methylbenzylamine on the mixture of the alkali metal salts of cis and trans β-phenylglycidic acids which are optionally prepared in situ.

* * * * *